US008620411B2

(12) United States Patent
Stamatas et al.

(10) Patent No.: US 8,620,411 B2
(45) Date of Patent: Dec. 31, 2013

(54) METHOD OF ASSESSING SKIN AND OVERALL HEALTH OF AN INDIVIDUAL

(75) Inventors: Georgios Stamatas, Somerset, NJ (US);
Nikiforos Kollias, Skillman, NJ (US);
Janeta Nikolovski, Princeton, NJ (US);
Benjamin Wiegand, Yardley, PA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 1880 days.

(21) Appl. No.: 10/986,941

(22) Filed: Nov. 15, 2004

(65) Prior Publication Data

US 2005/0203355 A1   Sep. 15, 2005

Related U.S. Application Data

(63) Continuation-in-part of application No. 10/735,188, filed on Dec. 12, 2003.

(51) Int. Cl.
*A61B 6/00* (2006.01)
(52) U.S. Cl.
USPC .......................................... 600/477; 600/476
(58) Field of Classification Search
None
See application file for complete search history.

(56) References Cited

U.S. PATENT DOCUMENTS

| 4,894,547 A | 1/1990 | Leffell et al. |
| 5,131,398 A | 7/1992 | Alfano et al. |
| 5,701,902 A | 12/1997 | Vari et al. |
| 6,091,985 A | 7/2000 | Alfano et al. |
| 6,721,582 B2 | 4/2004 | Trepagnier et al. |
| 2002/0016534 A1 * | 2/2002 | Trepagnier et al. ........... 600/316 |
| 2005/0049467 A1 | 3/2005 | Kollias et al. |

FOREIGN PATENT DOCUMENTS

WO    WO 03/073926 A    9/2003

OTHER PUBLICATIONS

Takema et al, "Age-related discontinuous changes in the in vivo fluorescence of human facial skin", Journal of Dermatological Science, vol. 15 (1997) pp. 55-58.
Monnier VM, Kohn RR, Cerami A: Accelerated age-related browning of human collagen in diabetes mellitus. *Proc Natl Acad Sci U S A* 81(2):583-587, 1984.
Doukas AG, Soukos NS, Babusis S, Appa Y, Kollias N: Fluorescence excitation spectroscopy for the measurement of epidermal proliferation. *Photochem Photobiol* 74(1):96-102., 2001.
Gillies R, Zonios G, Anderson RR, Kollias N: Fluorescence excitation spectroscopy provides information about human skin in vivo. *J Invest Dermatol* 115(4):704-707, 2000.
Glueck J. The Climate of Tucson, Arizona. NOAA Technical Memorandum NWS WR-249, Western Region, National Weather Service Office, National Oceanic and Atmospheric Administration, 1997.
Hormel SE, Eyre DR: Collagen in the ageing human intervertebral disc: an increase in covalently bound fluorophores and chromophores. *Biochim Biophys Acta* 1078(2):243-250, 1991.

(Continued)

*Primary Examiner* — Jacqueline Cheng

(57) ABSTRACT

The present invention relates to a method of determining skin health of an area of skin and overall health of an individual by exposing the area of skin to a first exposure radiation to induce the area of skin to emit a first fluorescent emission, measuring the intensity of the first fluorescent emission, exposing the area of skin to a second exposure radiation to induce the area of skin to emit a second fluorescent emission, measuring the intensity of the second fluorescent emission, calculating a ratio of these intensities, and comparing the ratio to a control ratio.

10 Claims, 11 Drawing Sheets

(56) References Cited

OTHER PUBLICATIONS

Kato Y, Kawakishi S, Aoki T, Itakura K, Osawa T: Oxidative modification of tryptophan residues exposed to peroxynitrite. *Biochem Biophys Res Commun* 234(1):82-84, 1997.
Kollias N, Gillies R, Moran M, Kochevar IE, Anderson RR: Endogenous skin fluorescence includes bands that may serve as quantitative markers of aging and photoaging. *J Invest Dermatol* 111(5):776-780, 1998.
Leffell DJ, Stetz ML, Milstone LM, Deckelbaum LI: In vivo fluorescence of human skin. A potential marker of photoaging. *Arch Dermatol* 124(10):1514-1518, 1988.
Monnier VM, Cerami A: Non-enzymatic glycosylation and browning of proteins in diabetes. *Clin Endocrinol Metab* 11(2):431-452, 1982.
Bellmunt MJ, Portero M, Pamplona R, Muntaner M, Prat J: Age-related fluorescence in rat lung collagen. *Lung* 173(3):177-185, 1995.
Brancaleon L, Durkin AJ, Tu JH, Menaker G, Fallon JD, Kollias N: In vivo fluorescence spectroscopy of nonmelanoma skin cancer. *Photochem Photobiol* 73(2):178-83., 2001.
Tian, WD, Anderson, R.R., Drake, L.A., Kollias, N., Noninvasive Monitoring of Treatment Related Changes in Psoriatic Plaques Using Fluorescence Excitation and Diffuse Reflectance Spectroscopy, Biomedical Optical Spectroscopy and Diagnostics, 1998 pp. 113-115.
Gonzalez, S., Zonios, G., Nguyen, B.C., Gillies, R. Kollias, N. Endogenous Skin Fluorescence is a Good Market for Objective Evaluation of Comedolysis, The Society for Investigative Dermatology, Inc. 2000, pp. 100-105.
Kollias, N. and Stamatas, G.N. Optical Non-Invasive Approaches to Diagnosis of Skin Diseases, The Society for Investigative Dermatology, Inc. 2002, pp. 64-75.
Brancaleon L, Lin G, Kollias N: The in vivo fluorescence of tryptophan moieties in human skin increases with UV exposure and is a marker for epidermal proliferation. *J Invest Dermatol* 113(6):977-982, 1999.
Monnier VM, Vishwanath V, Frank KE, Elmets CA, Dauchot P, Kohn RR: Relation between complications of type I diabetes mellitus and collagen-linked fluorescence. *N Engl J Med* 314(7):403-408, 1986.
Na R, Stender IM, Henriksen M, Wulf HC: Autofluorescence of human skin is age-related after correction for skin pigmentation and redness. *J Invest Dermatol* 116(4):536-540, 2001.
Njoroge FG, Fernandes AA, Monnier VM: Mechanism of formation of the putative advanced glycosylation end product and protein cross-link 2-(2-furoyl)-4(5)-(2-furanyl)-1H-imidazole. *J Biol Chem* 263(22):10646-10652, 1988.
Odetti P, Pronzato MA, Noberasco G, et al.: Relationships between glycation and oxidation related fluorescences in rat collagen during aging. An in vivo and in vitro study. *Lab Invest* 70(1):61-67, 1994.
Odetti PR, Borgoglio A, Rolandi R: Age-related increase of collagen fluorescence in human subcutaneous tissue. *Metabolism* 41(6):655-658, 1992.
Pongor S, Ulrich PC, Bencsath FA, Cerami A: Aging of proteins: isolation and identification of a fluorescent chromophore from the reaction of polypeptides with glucose. *Proc Natl Acad Sci U S A* 81(9):2684-2688, 1984.
Reihsner R, Melling M, Pfeiler W, Menzel EJ: Alterations of biochemical and two-dimensional biomechanical properties of human skin in diabetes mellitus as compared to effects of in vitro non-enzymatic glycation. *Clin Biomech (Bristol, Avon)* 15(5):379-86., 2000.
Sell DR, Monnier VM: Structure elucidation of a senescence cross-link from human extracellular matrix. Implication of pentoses in the aging process. *J Biol Chem* 264(36):21597-21602,1989.
Shaklai N, Garlick RL, Bunn HF: Nonenzymatic glycosylation of human serum albumin alters its conformation and function. *J Biol Chem* 259(6):3812-3817, 1984.
Stamatas GN, Wu J, Kollias N: Non-invasive method for quantitative evaluation of exogenous compound deposition on skin. *J Invest Dermatol* 118(2):295-302, 2002.
Tian WD, Gillies R, Brancaleon L, Kollias N: Aging and effects of ultraviolet A exposure may be quantified by fluorescence excitation spectroscopy in vivo. *J Invest Dermatol* 116(6):840-845, 2001.
Wolff SP, Dean RT: Glucose autoxidation and protein modification. The potential role of 'autoxidative glycosylation' in diabetes. *Bio000000chem J* 245(1):243-250, 1987.
Wu J, Feld MS, Rava RP: Analytical model for extracting intrinsic fluorescence in turbid media. *Applied Optics* 32(19):3585-3595, 1993.
Zhang JC, Savage HE, Sacks PG, et al.: Innate cellular fluorescence reflects alterations in cellular proliferation. *Lasers Surg Med* 20(3):319-31., 1997.
European Search Report dated Mar. 23, 2005, for corresponding EP application 04257677.7.

* cited by examiner

METHOD OF ASSESSING SKIN AND OVERALL HEALTH OF AN INDIVIDUAL

CROSS-REFERENCE TO RELATED APPLICATION

This application is a continuation-in-part of U.S. application Ser. No. 10/735,188, filed on Dec. 12, 2003. The complete disclosure of the aforementioned related U.S. patent application is hereby incorporated herein by reference for all purposes.

FIELD OF THE INVENTION

The present invention relates to a method of assessing skin and the overall health of an individual using fluorescence.

BACKGROUND OF THE INVENTION

The native fluorescence of human and mouse skin has been shown to vary with aging and UV exposure in a predictable manner. See Brancaleon et al., J. Invest. Dermatol. 113(6): 977-982, 1999; Kollias et al., J. Invest. Dermatol.111(5):776-780, 1998; Leffell et al., Arch Dermatol. 124(10):1514-1518, 1988; Na et al., J. Invest. Dermatol. 116(4):536-540, 2001; and Tian et al., J. Invest. Dermatol. 116(6):840-845, 2001. Thus, fluorescence spectroscopy has been proven to be an objective quantitative method for studying skin aging and photoaging.

The major fluorescence bands that have been detected by in vivo fluorescence spectroscopy include: a) a band assigned to tryptophan (maximum at 295 nm excitation, 345 nm emission), b) a band assigned to pepsin digestible collagen cross-links (335 nm excitation, 390 nm emission), c) a band assigned to collagenase digestible collagen cross-links (370 nm excitation, 460 nm emission), and d) a band most likely due to elastin and collagen cross-links (390-420 nm broad band excitation, 500 nm emission). See Gillies et al. J. Invest. Dermatol, 115(4):704-707, 2000. Secondary fluorescence bands have been identified that may be related to collagen peroxidation (Odetti et al. Lab Invest. 70(1):61-67, 1994) or elastin (Leffell et al., Arch Dermatol., 124(10):1514-1518, 1988): one at 356 nm excitation, 420 nm emission and another at 390 nm excitation, 460 nm emission respectively.

The fluorescence signal assigned to tryptophan moieties measured in situ was found to increase when epidermal proliferation increases. See Kollias et al., J. Invest. Dermatol, 111(5):776-780,1998 and Zhang et al., Lasers Surg. Med. 20(3):319-331, 1997. This was verified by inducing epidermal repair after mechanical insult, e.g. tape stripping. See Brancaleon et al., J. Invest. Dermatol. 113(6):977-982, 1999. Furthermore, α-hydroxy-acid-induced increases of cellular turnover in human epidermis caused the 295 nm excitation band to increase in a dose dependent manner. See Doukas et al., Photochem. Photobiol. 74(1):96-102, 2001. In SKH hairless mice the fluorescence due to tryptophan moieties decreases with age, implying an age-related reduction of the epidermal cell turnover rate. See Kollias et al., J. Invest. Dermatol. 111(5):776-780,-1998.

Non-enzymatic glycosilation of proteins occurs spontaneously with aging (See Monnier et al., Clin Endocrinol Metab 11(2):431-452, 1982; Njoroge et al., J. Biol. Chem. 263(22): 10646-10652, 1988; Sell et al., J. Biol Chem 264(36):21597-21602, 1989; and Shaklai et al., J. Biol Chem 259(6):3812-3817, 1984) resulting in increased protein absorbance and fluorescence (Maillard reaction). The glucose-protein adduct rearranges and dehydrates to form brown and fluorescent pigments, which may form cross-links resulting in decreased protein solubility and altered mechanical properties. Such cross-links are evident in long-lived proteins, such as elastin and collagen. The accumulation of fluorescing cross-links in collagen has been used as a marker for the observed accelerated rate of aging in diabetes. See Monnier et al., Clin. Endocrinol. Metab 11(2):431-452, 1982. In SKH mice the magnitude of the pepsin digestible collagen cross-link fluorescence maximum increases with chronological aging, whereas the increase in the magnitude of the collagenase digestible collagen cross-link and the elastin-associated fluorescence maxima is modest. See Kollias et al., J. Invest. Dermatol. 111(5):776-780, 1998. Similar trends have been observed in rats ex vivo (Odetti et al., Lab Invest. 70(1):61-67, 1994), in human buttock skin in vivo (Na et al., J. Invest. Dermatol 116(4):536-540, 2001), and in ex vivo human dermis taken from skin around the operating area of patients undergoing vascular surgery (Odetti et al., Metabolism 41(6)655-658, 1992).

Applicants have surprisingly found that skin native autofluorescence is a tool to evaluate skin health and the effects of aging (e.g., chronological aging as well as photoaging) on skin health.

SUMMARY OF THE INVENTION

In one aspect, the present invention features a method of determining skin health of an area of skin by (i) exposing the area of skin to a first exposure radiation to induce the area of skin to emit a first fluorescent emission, wherein the first exposure radiation comprises primarily of wavelengths of from about 290 nm to about 300 nm; (ii) measuring the intensity of the first fluorescent emission having a wavelength of from about 320 to about 350; (iii) exposing the area of skin to a second exposure radiation to induce the area of skin to emit a second fluorescent emission, wherein the second exposure radiation comprises primarily of wavelengths of from about 330-420 nm; (iv) measuring the intensity of the second fluorescent emission having a wavelength of from about 380-470; (v) calculating a ratio of the intensity measured in step (ii) to the intensity measured in step (iv); and (vi) comparing the ratio to a control ratio.

In another aspect, the present invention features a method of determining the effect of a treatment to the skin of a subject by: (i) exposing a first area of skin to a first exposure radiation to induce the area of skin to emit a first fluorescent emission, wherein the first exposure radiation comprises primarily of wavelengths of from about 290 nm to about 300 nm and wherein the first area of skin was exposed to the composition; (ii) measuring the intensity of the first fluorescent emission having a wavelength of from about 320 to about 350;(iii) exposing the first area of skin to a second exposure radiation to induce the area of skin to emit a second fluorescent emission, wherein the second exposure radiation comprises primarily of wavelengths of from about 330-420 nm; (iv) measuring the intensity of the second fluorescent emission having a wavelength of from about 380-470; (v) calculating a ratio of the intensity measured in step (ii) to the intensity measured in step (iv);(iv) repeating steps (i) to (v) for a second area of skin, wherein the second area of skin was not exposed to the composition; and (vii) comparing the ratio for the first area of skin to the ratio for the second area of skin.

In a third aspect, the present invention relates to a method of assessing the overall health of an individual including creating a standard curve for a plurality of healthy individuals by I) exposing an area of skin of each healthy individual to a first exposure radiation to induce said area of skin to emit a first fluorescent emission, wherein said first exposure radiation comprises primarily of wavelengths of from about 290 nm to about 300 nm; II) measuring the intensity of said first fluorescent emission having a wavelength of from about 320 nm to about 350 nm; (III) exposing said area of skin to a second exposure radiation to induce said area of skin to emit a second fluorescent emission, wherein said second exposure radiation comprises primarily of wavelengths of from about 330 nm to about 420 nm; IV) measuring the intensity of said second fluorescent emission having a wavelength of from about 380 nm to about 470 nm; V) calculating a ratio of said intensity measured in step (II) to said intensity measured in step (IV); plotting a standard curve for age of individual versus the ratio of step V; performing the measurements of steps II and IV for an individual; calculating the ratio of step V for the individual; and comparing the ratio of step V for the individual in question to the standard curve to determine the overall health of the individual.

Alternatively, the average fluorescence value by age can be determined by following the same steps described above. The fluorescence value of an individual whose overall health is in question may then be compared to the average fluorescence value for that age. If the fluorescence value of the individual is below the average fluorescence value for the age, it is an indication that there may be a health problem, such as diabetes.

DETAILED DESCRIPTION OF THE INVENTION

Figure 1:
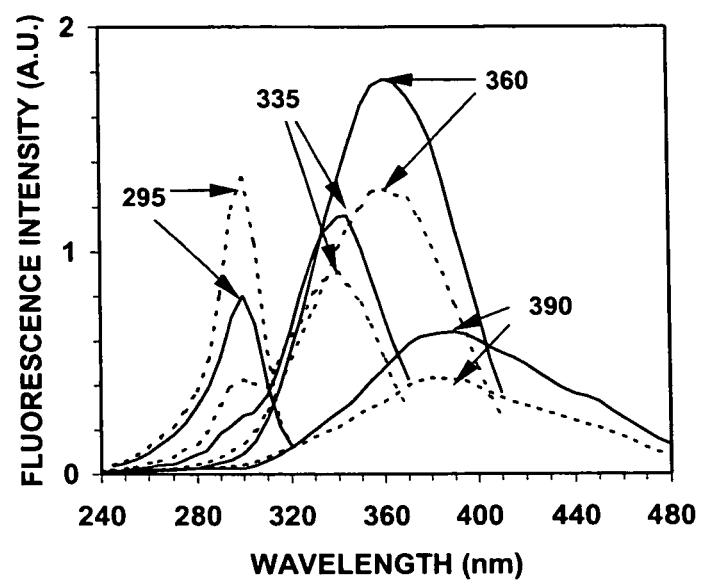
FIG. 1 is a graph showing the excitation spectra of two individuals of 30 (dotted lines) and 60 (solid lines) years of age, respectively.
Figure 2A:
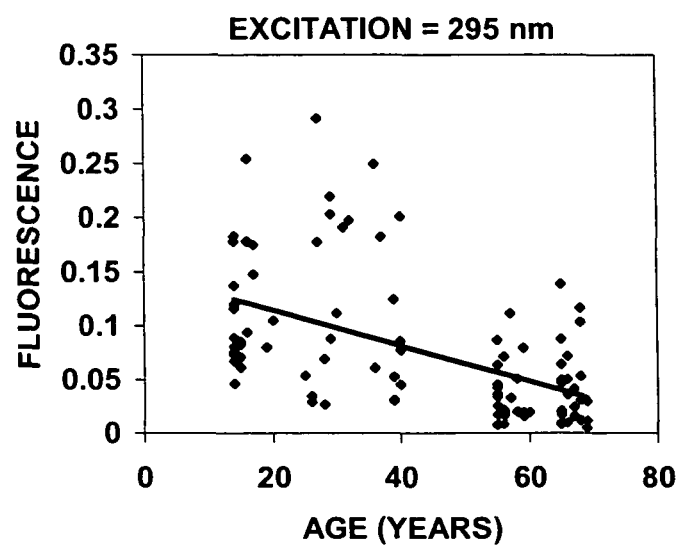
FIG. 2a is a graph showing the age distribution of the fluorescence intensity for the 295 nm excitation band.
Figure 2B:
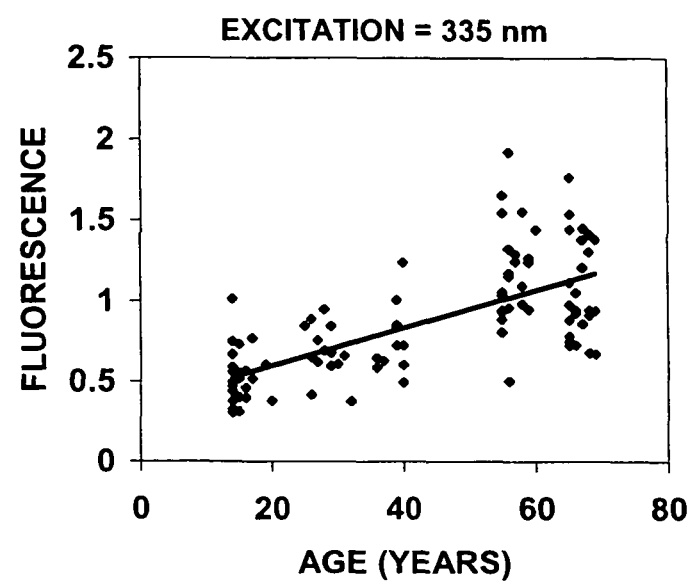
FIG. 2b is a graph showing the age distribution of the fluorescence intensity for the 335 nm excitation band.
Figure 2C:
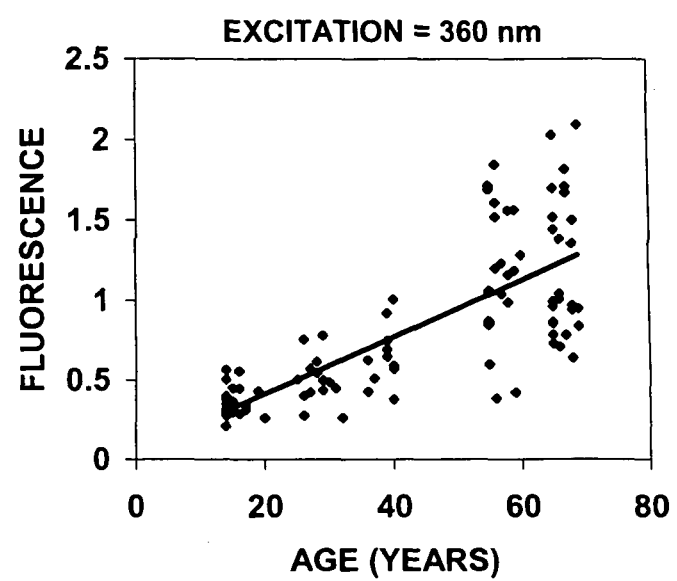
FIG. 2c is a graph showing the age distribution of the fluorescence intensity for the 360 nm excitation band.
Figure 2D:
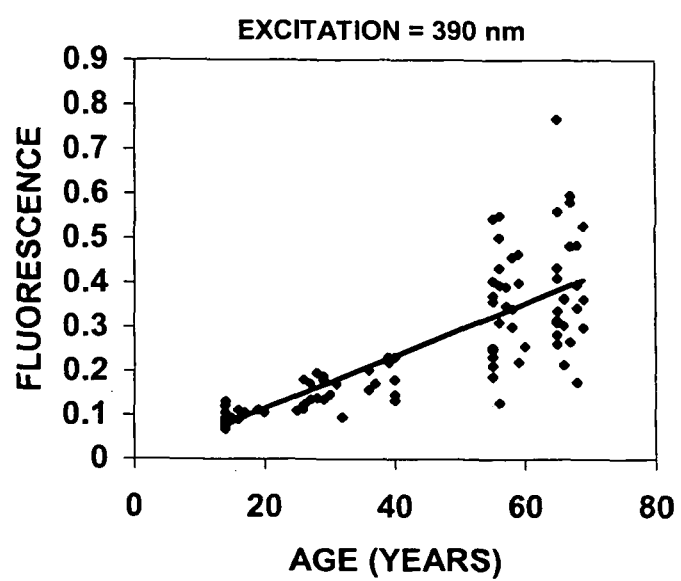
FIG. 2d is a graph showing the age distribution of the fluorescence intensity for the 390 nm excitation band.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Exposure Radiation

In one embodiment, the area(s) of skin are exposed to at least two exposure radiations (e.g., from UV radiation sources such as xenon arc lamps or mercury lamps). In one embodiment, the first exposure radiation includes primarily wavelengths of from about 290 nm to about 300 nm and the second exposure radiation includes primarily wavelengths of from about 330-420 nm. What is meant by "primarily" is at least half of the wavelengths of the exposure radiation. In a further embodiment, the first exposure radiation includes primarily wavelengths of about 295 nm and the second exposure radiation includes primarily wavelengths of from about 390 to about 410 nm.

The exposure radiations are directed to the skin in order emit a fluorescent emission and to measure the intensity of such emission (e.g., a specific wavelength or wavelength range). In one embodiment, the method includes measuring the intensity of the first fluorescent emission having a wavelength of from about 330 nm to about 350 nm (e.g., about 340 nm) and measuring the intensity of the second fluorescent emission having a wavelength of from about 380 nm to about 470 nm (e.g., 440 nm).

The ratio of the two intensities measured above can be calculated and compared to a control ratio. What is meant by control ratio is an established standard ratio (e.g., an established norm for the subject's age, sex, and/or race) or a ratio obtained from the subject (e.g., previously obtained from the same area of skin or obtained from another area skin such as an area of skin not readily exposed to UV radiation such as the underarm or buttocks). The method, thus, is able to determine the skin health of the subject (e.g., by comparing the ratio to the control ratio). The difference of the ratio value between exposed areas of skin and protected areas of skin has been found to generally decline with age. This difference is believed to be indicative of the ability of skin to react to external stimuli by repairing itself. Therefore, higher ratio values of the exposed areas compared to the unexposed areas is believed to be an indication of healthy skin, able to regenerate itself. Furthermore, high ratio values of the exposed site compared to the unexposed site is also believed to be indicative of the youthfulness of the skin.

In one embodiment, the method is used to determine the effect of effect of a treatment to the skin of a subject. Examples of such treatments include, but are not limited to, cosmetic and pharmaceutical treatments (e.g, topical, parenteral, or oral), laser treatment, or abrasive treatment (e.g., microderm abrasion). In one embodiment, the treatment is a topical composition, such as a topical lotion or cream containing an anti-aging agent such as a retinoid (e.g., retinoic acid or retinol).

Applicants have found that while the fluorescence due to tryptophan moieties was found to decrease monotonically with age, the fluorescence bands assigned to pepsin and collagenase digestible collagen cross-links as well as that due to elastin cross-links was found to increase. These trends were surprisingly found to be independent of geographical region and seasonal effects. Similar trends were also observed in sun-protected areas. A marker that strongly correlates with skin aging, based on the ratio of the fluorescence intensity due to tryptophan moieties (centered at 295 nm excitation) to the fluorescence intensity assigned to collagen and elastin cross-links (centered at 390 nm excitation), was also found. This marker, "Normalized tryptophan fluorescence," was found to decrease with aging, and photoaging was found to accelerate the rate of the decrease. Normalized tryptophan fluorescence was also shown to be able to be used to monitor the effects of anti-aging treatments.

Fluorescence Measurements

In vivo fluorescence spectroscopy can be performed for example using a fiber optic probe attached to a spectrofluorimeter (e.g. the model SkinSkan (JY Horiba, Edison, N.J.)). The method requires: a) a UV radiation source (e.g., a Xenon arc lamp or a mercury lamp), b) a method of selecting the radiation wavelength (e.g. a monochromator, a prism, or a grating), c) a method of delivery of the radiation to the tissue (e.g. a fiber bundle), d) a method of collection of the emitted radiation from the tissue (e.g. a fiber bundle), e) a method of selecting the emitted radiation wavelength (e.g. a monochromator, a prism, or a grating), and f) a method of detecting the emitted radiation (e.g. a photomultiplier, a single photodiode, a photodiode array, or a CCD array). See, e.g., Stamatas G N, et al., *J Invest Dermatol* 118(2):295-302, 2002.

Measurements were preformed by placing the fiber optic probe in contact with the skin site of interest. Before each set of measurements, the instrument was spectrally calibrated for excitation and emission in the region 250-650 nm. The chromatic resolution of the spectrofluorimeter was ±1 nm.

Acquisition of excitation spectra was the preferred method of measuring in vivo skin fluorescence. The reason for this choice over acquisition of emission spectra was that excitation spectra were similar to absorption spectra and bands tend to be narrower than in emission acquisition, both of which help in the identification of the individual fluorophores in a complex spectrum. The excitation spectra that were used in this study were the following: a) excitation scanned from 240 nm to 320 nm with emission set at 340 nm (tryptophan excitation maximum at 295 nm), b) excitation scanned from 240 nm to 380 nm with emission set at 390 nm (pepsin digestible collagen cross-link excitation maximum at 335 nm), c) excitation scanned from 240 nm to 410 nm with emission at 420 nm (collagenase digestible collagen cross-link excitation maximum at 360 nm), d) excitation scanned from 260 nm to 490 nm with emission set at 500 nm (elastin cross-links—desmosine and isodesmosine—excitation maximum at about 390 nm).

In order to account for variations in skin native pigmentation that attenuates the detected fluorescence signal, fluorescence intensity was normalized with the diffuse reflectance signal of the same skin site at the corresponding wavelength. See, e.g., Stamatas G N, et al., *J Invest Dermatol* 118(2):295-302, 2002. A diffuse reflectance spectrum can be acquired by synchronizing the excitation and emission monochromators to select the same wavelength, scanning the range from 240 nm to 500 nm. The correction was necessary especially for wavelengths greater than 315 nm. The measured fluorescence in this wavelength region arises from the dermis (Gillies et al, 2000, Kollias et al, 1998), which means that excitation light has to travel through the whole epidermis where it is attenuated by epidermal melanin and proteins, both of which absorb strongly in the UV. Then the emitted light has to travel again through the whole epidermis to the collection fibers. This means that both excitation and emission intensities are compromised. On the other hand, for fluorophores that reside in the epidermis, i.e. signals for excitation wavelengths less than 315 nm (Gillies R, et al., *J Invest Dermatol* 115(4):704-707, 2000), the attenuation effect is not as severe. Furthermore, the intensity of the light source is low below 300 nm and normalization of the fluorescence by the diffuse reflectance signal in this wavelength range amplified the noise. This problem arises only for the tryptophan band (295 nm excitation). To overcome this problem, the tryptophan fluorescence signal may be normalized to another fluorescence band, rather than to the diffuse reflectance value at 295 nm. Normalizing the tryptophan band to the 390 nm excitation band was used since the latter was found to change the slowest with aging. Other bands can also be used for the normalization. Also if the radiation source intensity is sufficient at about 295 nm normalization with the diffuse reflectance signal at this wavelength can be used.

Clinical Studies

To study the effects of aging on the native fluorescence of human facial skin, spectra was acquired from the cheek area of 522 healthy individuals with ages 15-75 years native to five different geographical locations of the Asia—Pacific region: a) Guangzhou, China, b) Harbin, China, c) Shanghai, China, d) Sendai, Japan, and e) Manila, Philippines. In order to identify potential seasonal effects, facial fluorescence from the same individuals was measured in summer and in winter at two locations (Harbin and Shanghai). All subjects were of skin type II-IV.

To investigate whether the observed changes on facial skin fluorescence were due to chronological aging or sun exposure (photoaging), a second set of measurements were conducted. Skin fluorescence was measured on the upper inner arm ("unexposed site") as well as the cheek area of 45 healthy subjects with ages 22-63 years. All subjects were of skin type II-IV. The study was conducted in Skillman, N.J. in the month of October.

In a third set of experiments, the effect of retinol on facial skin fluorescence was studied. Twenty healthy individuals of Caucasian descent (skin types II-III) with ages 50-70 years were asked to apply a cream formulation containing 0.15% retinol containing a broad band spectrum SPF 15 sunscreen on one side of the face and a matched SPF 15 vehicle control (no retinol) on the other side daily. Active and vehicle were randomly assigned to each side of the face of every subject. The participants of the study, as well as the investigators, were blind to the assignment code. The study was carried out in Tucson, Ariz. and commenced in February. Fluorescence excitation spectra were acquired at baseline, at three months, and at six months from both cheeks and from the upper inner arm as untreated sun-protected control. Diabetic patients were excluded as this condition may interfere with the fluorescence measurements.

Data Analysis

Linear regressions of the data were calculated using the least square errors algorithm. The goodness of fit is given by the correlation coefficient ($R^2$). Statistical significance was calculated using the Student's t-test for paired data distributions.

Results

The intensity of skin fluorescence was found to change with age. A series of typical excitation spectra taken on the cheek area of two individuals of 30 and 60 years of age, both of skin type II is shown in FIG. 1. In general, the fluorescence excitation band ascribed to the tryptophan moieties (295 nm) decreases with age, whereas the bands of collagen and elastin cross-links (335 nm, 360 nm, and 390 nm) increase.

The age distribution of the fluorescence intensity for the 295 nm, 335 nm, 360 nm, and 390 nm excitation bands taken from 108 individuals in Shanghai, China is shown in FIGS. 2a, 2b, 2c, and 2d correspondingly. The data has been fitted with linear regressions and the intervals between the average±one standard deviation are shown. It is evident that the value of the standard deviation of the data distribution was higher for younger ages for the 295 nm excitation band. The opposite was found for all the other bands. The 295 nm excitation band was the only one declining with age (at −0.002 units/year). All the bands ascribed to collagen or elastin cross-links increased, indicating accumulation of extracellular matrix cross-links with age. From these bands, the 390 nm band showed the slowest increase with age (0.005 units/year). The correlation coefficient ($R^2$) was best for the 390 nm band (0.61) followed by the bands 360 nm (0.55), 335 nm (0.41), and 295 nm (0.32).

The same trends were observed independent of geographical area, skin type, or season of measurements. The slopes of the best linear fit of the data represent the rates of change of the fluorescence intensities and are shown in Table I. Rates of change (units/year) for the skin fluorescence bands and the normalized tryptophan fluorescence ($I_{295\,nm}/I_{390\,nm}$). All measurements were preformed on the face (cheek). The rates of change were calculated from the slopes of the best linear fit of the data. The values are given in fluorescence units per year for the fluorescence bands and in ratio units per year for the normalized tryptophan fluorescence. PDCXL=pepsin digestible collagen cross-links, CDCXL=collagenase digestible collagen cross-links, NTF=normalized tryptophan fluorescence.

Figure 3:
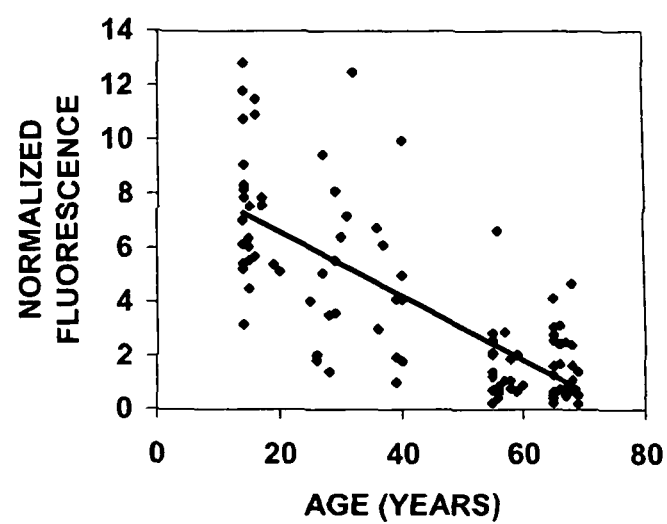
FIG. 3 is a graph showing the age distribution of the florescence intensity for 295 nm excitation band normalized to the fluorescence intensity of the 390 nm excitation band.
Figure 4A:
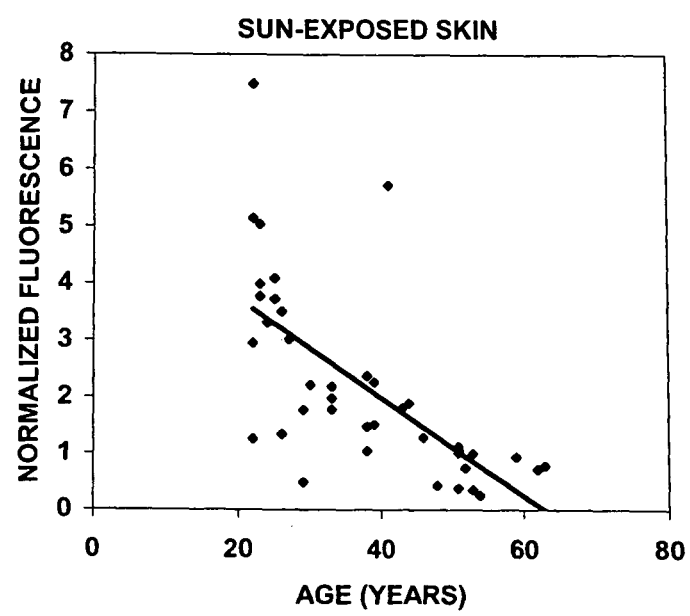
FIG. 4a is a graph showing the age distribution of the normalized florescence intensity for a sun-exposed area of the skin.
Figure 4B:
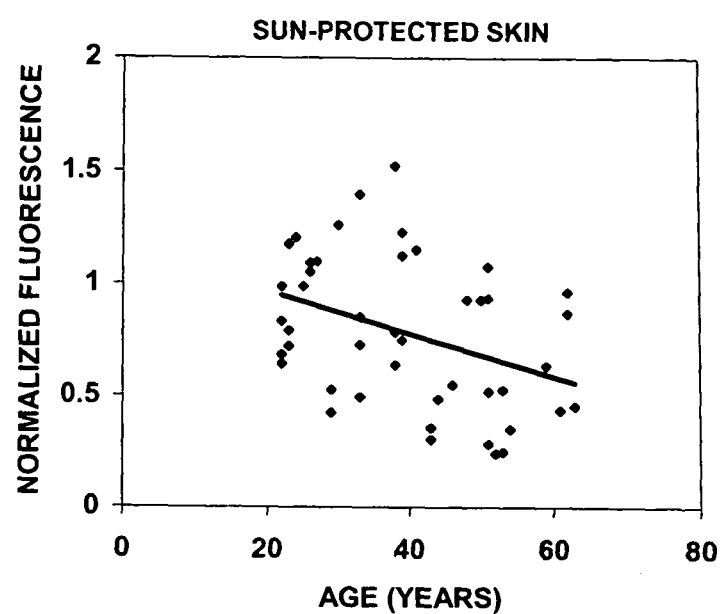
FIG. 4b is a graph showing the age distribution of the normalized florescence intensity for a sun-protected area of the skin.

(photoaging) affected the observed decrease of the normalized tryptophan fluorescence with age, measurements were performed on the upper inner arm (relatively unexposed site) as well as on the cheek (sun-exposed site) of 45 volunteers. The results are shown in FIGS. 4a and 4b. In accordance with the data presented in FIG. 3, the fluorescence ratio $I_{295\,nm}/I_{390\,nm}$ acquired from the face decreased with age (FIG. 4a). The rate of decrease (0.087 units/year) was close to the values from other regions noted in Table I. For the sun-protected site the normalized tryptophan fluorescence was also decreasing with age (FIG. 4b), although at a much slower rate (0.010 units/year).

Figure 5A:
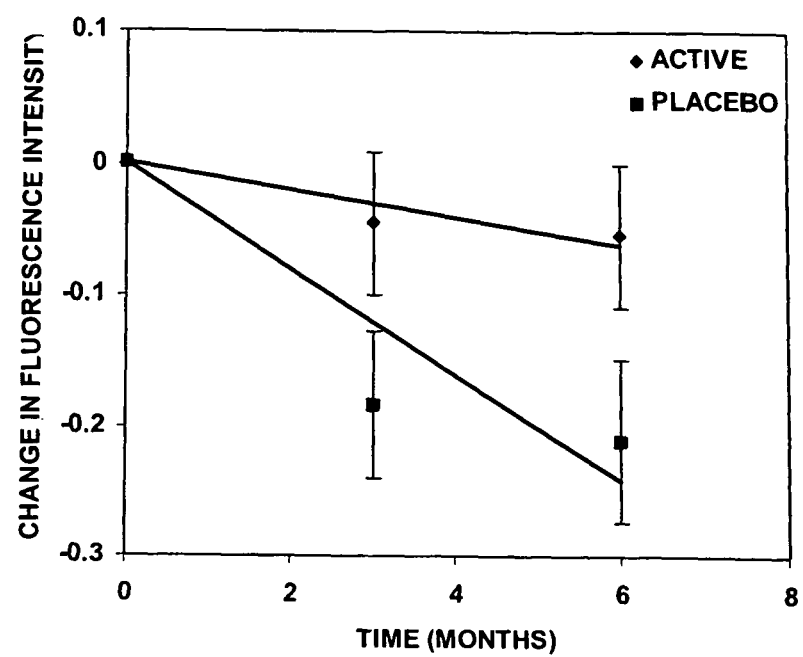
FIG. 5a is a graph showing the change in fluorescence intensity over time at 295 nm excitation for retinol (active) and placebo treated skin.
Figure 5B:
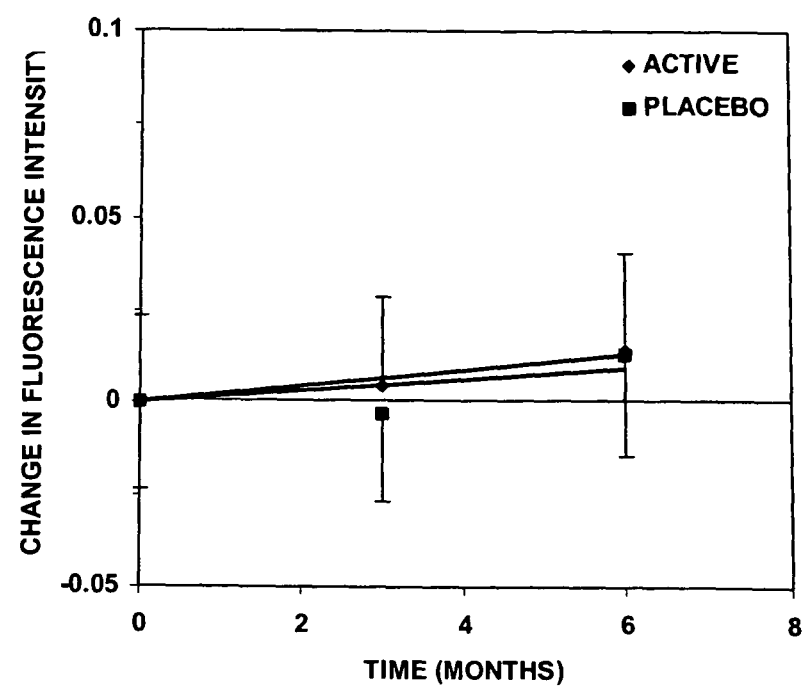
FIG. 5b is a graph showing the change in fluorescence intensity over time at 390 nm excitation for retinol (active) and placebo treated skin.
Figure 5C:
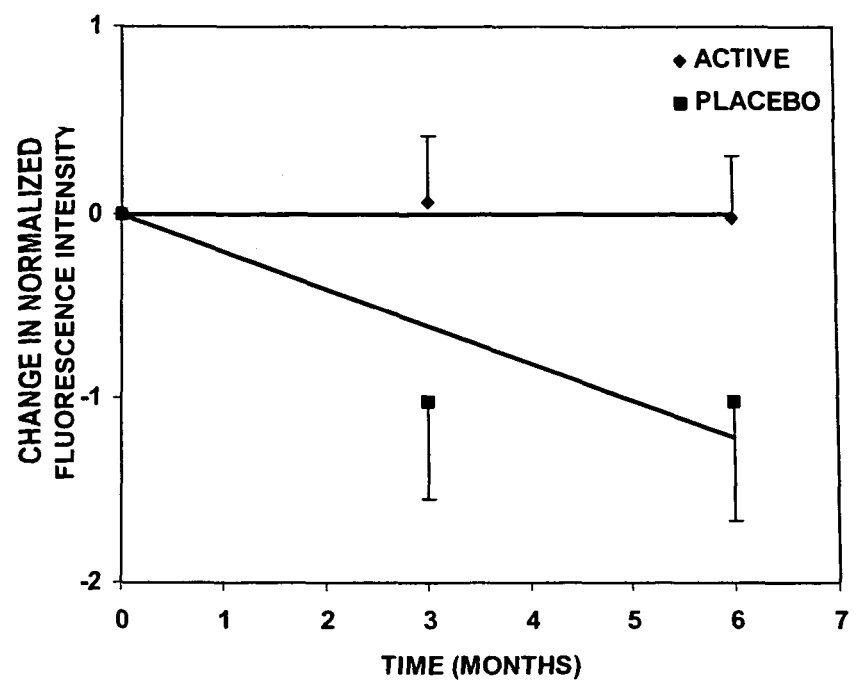
FIG. 5c is a graph showing normalized florescence intensity over time for for retinol (active) and placebo treated skin.

In vivo skin fluorescence measurements was used to follow the anti-aging effects of topical treatment with retinol. The results for the cheek sites treated with the formulation containing 0.15% retinol or the vehicle formulation are shown in FIGS. 5a, 5b, and 5c. Both groups demonstrated a typical decrease in the 295 nm band fluorescence (FIG. 5a), although the rate of decrease was significantly less for the cheeks that received retinol treatment (−0.01 units/month for the active treated group versus −0.04 units/month for the placebo treated group). The 390 nm band did not significantly change over the period of the study, although a slight increasing trend

TABLE I

| Geographical Area | Season | n | Tryptophan 295 nm | PDCXL 335 nm | CDCXL 360 nm | Elastin 390 nm | NTF Ratio 295 nm/390 nm |
|---|---|---|---|---|---|---|---|
| Guangzhou, China | Summer | 108 | −0.0021 | 0.010 | 0.013 | 0.0053 | −0.103 |
| Harbin, China | Summer | 106 | −0.0007 | 0.012 | 0.015 | 0.0062 | −0.074 |
| Harbin, China | Winter | 64 | −0.0025 | 0.014 | 0.016 | 0.0047 | −0.091 |
| Shanghai, China | Summer | 100 | −0.0017 | 0.012 | 0.018 | 0.0060 | −0.119 |
| Shanghai, China | Winter | 100 | −0.0024 | 0.012 | 0.013 | 0.0053 | −0.135 |
| Sendai, Japan | Summer | 108 | −0.0019 | 0.010 | 0.016 | 0.0047 | −0.128 |
| Manila, Philippines | Summer | 100 | −0.0003 | 0.002 | 0.010 | 0.0060 | −0.038 |
| Skillman, NJ, USA | Fall | 45 | −0.0773 | 0.008 | 0.006 | 0.0063 | −0.088 |

In all geographic regions where the study took place and independent of the season, the fluorescence intensity of the tryptophan band decreased with age, while the intensities of the other three bands increased. Furthermore, the values of the slopes were fairly close together within the limits of uncertainty.

Normalizing the fluorescence intensity value of the 295 nm band to any of the other three bands resulted in a fluorescence marker that was relatively independent of skin pigmentation. Furthermore, since the intensity of the 295 nm band decreased, while the intensities of the bands ascribed to cross-links increased with age, the above mentioned ratio resulted in stronger age dependence. The ratio that resulted in the strongest age dependence was that of the fluorescence intensity of the 295 nm band ($I_{295\,nm}$) over the fluorescence intensity of the 390 nm band ($I_{390\,nm}$). The age distribution of the normalized tryptophan fluorescence ($I_{295\,nm}/I_{390\,nm}$) for Shanghai, China is shown in FIG. 3. In all these figures the data has been fitted with linear regressions and the intervals between the average±one standard deviation are provided. The standard deviation of the data distribution was higher for younger ages, however there was no significant correlation of the coefficient of variance (mean/standard deviation) with age. The correlation coefficient values were 0.4-0.5 for all places with the exception of Manila ($R^2 = 0.15$).

The cheek area was selected as it was expected to have received solar UV radiation that results in cumulative skin damage over a lifetime. To investigate whether sun exposure was evident in both active and placebo treated groups (FIG. 5b). Normalization of the tryptophan fluorescence band to the 390 nm excitation band (FIG. 5c) showed that the decrease of the 295 nm band in the retinol treated group was most likely due to pigmentation increase in the subjects over the period of the study (note that the study took place between February and July). The rate of change in the normalized tryptophan fluorescence values in the vehicle treated group was −0.062±0.029 ratio units per month. For the sites receiving retinol treatment, the decrease of the intensity of the 295 nm band was attenuated significantly compared to vehicle treated sites ($p<0.01$). The normalized tryptophan fluorescence values remained virtually constant for the retinol treated sites, significantly different ($p<0.05$) from the corresponding values for the sites that received vehicle treatment.

Measurements acquired on the upper inner arm (untreated) of the individuals at times 0, 3, and 6 months of the study demonstrated that the normalized tryptophan fluorescence values were decreasing, although at a much slower rate than the placebo treated skin in accordance with the data shown in FIG. 4b. The anti-aging effects of retinol treatment measured with fluorescence were in agreement with visual observations of reduction in the appearance of wrinkles in the treated areas. Treatment with vehicle cream alone did not have an effect on the appearance of wrinkles.

In a separate study, an age dependent curve of the facial skin fluorescence from healthy individuals (normalized tryptophan fluorescence or "NTF") was established.

Nine healthy and thirteen type II diabetic (self declared) volunteers were recruited to participate in the fluorescence measurement study with ages 45-60 years. For the diabetic population tested, the HbAlc values ranged from 5.7 to 8.1. Fluorescence spectra were acquired on the ventral arm of all the volunteers.

Fluorescence acquisition consisted of a synchronous scan of excitation and emission wavelengths in the range 250-600 nm with constant Stokes shift of 50 nm and was preformed with a spectrofluorimeter (model SkinSkan, JY Horiba, Edison, N.J.). This scan provides information for the tryptophan fluorescence (excitation 295 nm, emission 345 nm) and for the collagen and elastin cross-link related fluorescence, including the band where the tryptophan fluorescence is normalized to (excitation 390 nm, emission 440 nm).

The normalized tryptophan fluorescence values measured on the control group (mean +/− one standard deviation=2.94 +/− 1.94) was higher than the diabetic group (mean+/− one standard deviation=0.85 −/+ 0.45). The low numbers of NFT for the diabetic group indicates a reduced capacity for epidermal repair compared to the control healthy group.

The reduced NTF values in diabetic skin may be related to the poor wound healing and repair capacity of diabetic skin. The data (Table 2) were compared with previous plotted data. Based on the NTF values from the "exposed" areas collected from the previous study it was demonstrated that the control group falls within the age-matched "healthy" curve, while the diabetic group assumes lower values.

A correlation between the NTF values and the HbAcl values of the participants was graphed. There is a definite trend that higher HbAcl values are related to high NTF values. The correlation need not be very strong as the two parameters are indicators of diabetes and not necessarily directly related with a cause-effect relation.

The difference between the NTF value of a diabetic from the average NTF value of the age-matched control group correlates roughly with the HbAcl value of the diabetic patient as shown in Table 3. Therefore the NTF value is indicative of the progression of the diabetes.

TABLE 2

|  | Age | n | NTF value |
|---|---|---|---|
| Control* | 16.6 ± 1.9 | 19 | 7.5548 ± 3.7455 |
| Control* | 36.1 ± 2.4 | 20 | 4.4387 ± 2.0563 |
| Control* | 57.8 ± 1.8 | 20 | 2.4180 ± 1.4281 |
| Control* | 69.2 ± 3.0 | 22 | 2.0012 ± 1.3322 |
| Control** | 48.1 ± 6.4 | 9 | 2.9455 ± 1.9440 |
| Diabetics** | 51.5 ± 3.6 | 13 | 0.8481 ± 0.4467 |

*cheek;
**forearm

TABLE 3

| HbAlc(%) | NTF difference from control |
|---|---|
| 5.7 | 1.7681 |
| 6.2 | 2.3265 |
| 6.2 | 2.1470 |
| 6.4 | 2.2231 |
| 6.5 | 1.5200 |
| 6.8 | 2.2914 |
| 7.2 | 2.5223 |
| 7.3 | 2.1321 |
| 7.5 | 1.8445 |
| 7.7 | 2.6253 |
| 8.1 | 2.4168 |

The data indicate that overall health of an individual may be assessed by creating a standard curve for healthy individuals and comparing the ratio for individual whose health is in question to those on the curve. As indicated above, a ratio that falls below the standard curve may be an indication that the individual has a health problem, such as diabetes.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of assessing skin health, effects of aging, photoaging, or diabetic condition of a subject in question, said method comprising:
    a. creating a control ratio by
        (I) exposing a first area of skin not readily exposed to UV radiation of the subject in question to a first exposure radiation to induce said first area of skin to emit a first fluorescent emission, wherein said first exposure radiation comprises primarily of wavelengths of from about 290 nm to about 300 nm;
        (II) measuring the intensity of said first fluorescent emission having a wavelength of from about 320 nm to about 350 nm to determine the amount of tryptophan in the skin;
        (III) exposing said first area of skin to a second exposure radiation to induce said first area of skin to emit a second fluorescent emission, wherein said second exposure radiation comprises primarily of wavelengths of from about 330 nm to about 420 nm;
        (IV) measuring the intensity of said second fluorescent emission having a wavelength of from about 380 nm to about 470 nm to determine the amount of collagen cross-links in the skin;
        (V) calculating a ratio of said intensity measured in step (II) to said intensity measured in step (IV) to form a control ratio that cancels the effect of pigmentation to get a first tryptophan fluorescence parameter related to health and independent of pigmentation;
    b. performing the measurements of steps (I), (II), (III) and (IV) for the subject in question on a second area of skin readily exposed to UV radiation;
    c. calculating a ratio of the intensity measurements of step (II) of step b to the intensity measurement of step (IV) of step b for the subject in question to form a test ratio that cancels the effect of pigmentation to get a second tryptophan fluorescence parameter related to health and independent of pigmentation; and
    d. comparing said test ratio to said control ratio to determine the skin health, effects of aging, photoaging, or diabetic condition of the subject in question.

2. A method of assessing skin health, effects of aging, photoaging, or diabetic condition of a subject in question, said method comprising:
    a. creating a standard curve for a plurality of healthy individuals by, for each healthy individual:
        (I) exposing an area of skin of each healthy individual to a first exposure radiation to induce said area of skin to emit a first fluorescent emission, wherein said first exposure radiation comprises primarily of wavelengths of from about 290 nm to about 300 nm;
        (II) measuring the intensity of said first fluorescent emission having a wavelength of from about 320 nm to about 350 nm to determine the amount of tryptophan in the skin;

(III) exposing said area of skin to a second exposure radiation to induce said area of skin to emit a second fluorescent emission, wherein said second exposure radiation comprises primarily of wavelengths of from about 330 nm to about 420 nm;

(IV) measuring the intensity of said second fluorescent emission having a wavelength of from about 380 nm to about 470 nm to determine the amount of collagen cross-links in the skin;

(V) calculating a ratio of said intensity measured in step (II) to said intensity measured in step (IV) to cancel the effect of pigmentation to get a tryptophan fluorescence parameter related to health and independent of pigmentation;

(VI) plotting a standard curve for age of healthy individual versus the ratio of step (V);

b. performing the measurements of steps (I), (II), (III) and (IV) for a subject in question who is not a member of the plurality of healthy individuals in (a); and c. calculating a ratio of said intensity measured in step (II) to said intensity measured in step (IV) for the subject in question to cancel the effect of pigmentation to get a tryptophan fluorescence parameter related to health and independent of pigmentation; and d. comparing the ratio for the subject in question to the ratio plotted in the standard curve to determine the skin health, effects of aging, photoaging, or diabetic condition of the subject in question.

3. The method of claim 2, wherein said first exposure radiation comprises primarily of wavelengths of about 295 nm.

4. The method of claim 3, wherein said step (II) comprises measuring the intensity of said first fluorescent emission having a wavelength of about 340 nm.

5. The method of claim 4, wherein said second exposure radiation comprises primarily of wavelengths of from about 390 nm to about 410 nm.

6. The method of claim 5, wherein said step (IV) comprises measuring the intensity of said second fluorescent emission having a wavelength of about 440 nm.

7. The method of claim 3, wherein said second exposure radiation comprises primarily of wavelengths of from about 390 nm to about 410 nm.

8. The method of claim 7, wherein said step (IV) comprises measuring the intensity of said second fluorescent emission having a wavelength of about 440 nm.

9. The method of claim 2, wherein said second exposure radiation comprises primarily of wavelengths of from about 390 nm to about 410 nm.

10. The method of claim 9, wherein said step (IV) comprises measuring the intensity of said second fluorescent emission having a wavelength of about 440 nm.

* * * * *